(12) United States Patent
Vasishtha

(10) Patent No.: US 10,278,854 B2
(45) Date of Patent: May 7, 2019

(54) DEVICE FOR APPLYING PRESSURE TO BONES OF ARM AND METHOD OF TREATMENT

(71) Applicant: Deepak Vasishtha, New York, NY (US)

(72) Inventor: Deepak Vasishtha, New York, NY (US)

(73) Assignee: Deepak Vasishtha, New York, NY (US)

( * ) Notice: Subject to any disclaimer, the term of this patent is extended or adjusted under 35 U.S.C. 154(b) by 600 days.

(21) Appl. No.: 14/808,552

(22) Filed: Jul. 24, 2015

(65) Prior Publication Data

US 2016/0022465 A1    Jan. 28, 2016

Related U.S. Application Data

(60) Provisional application No. 62/029,341, filed on Jul. 25, 2014.

(51) Int. Cl.
*A61F 5/01* (2006.01)
*A61H 1/00* (2006.01)

(52) U.S. Cl.
CPC ............ *A61F 5/013* (2013.01); *A61H 1/008* (2013.01); *A61H 2201/1418* (2013.01); *A61H 2201/1635* (2013.01); *A61H 2205/065* (2013.01)

(58) Field of Classification Search
CPC .......... A61F 5/0118; A61F 5/013; A61F 5/37; A61F 5/3715; A61F 5/3723; A61F 5/3761; A61F 5/05858; A61F 5/05866; A61F 5/32; A61F 5/01; A61F 5/0102; A61F 5/05; A61F 5/058; A61F 5/30; A61F 5/34;

(Continued)

(56) References Cited

U.S. PATENT DOCUMENTS 5,441,058 A    8/1995    Fareed
5,468,220 A    11/1995   Sucher
(Continued)

FOREIGN PATENT DOCUMENTS

EP    2808237 A1    12/2014

OTHER PUBLICATIONS

International Search Report and Written Opinion for PCT/US20151041959 dated Nov. 3, 2015, 12 pgs.
(Continued)

*Primary Examiner* — Alireza Nia
*Assistant Examiner* — Rachel A Berezik
(74) *Attorney, Agent, or Firm* — Procopio, Cory, Hargreaves & Savitch LLP

(57) ABSTRACT

A device for applying pressure to a bone of a human arm. The device includes a flexible member having first and second ends, a linear member fixed to the first end and slidingly coupled to the second end, a cam coupled to one end of the linear member and contacting a surface of the second end, and a lever arm coupled to the cam. The lever arm being movable between: a first position in which the cam to apply a first pressure to the surface of the second end of the flexible member; and a second position in which cam applies a second, larger pressure to the surface of the second end of the flexible member causing the second end of the flexible member to move relative to one end of the linear member and reduce a distance between the first end and second ends of the flexible member.

13 Claims, 14 Drawing Sheets

(58) Field of Classification Search
CPC ...... A61H 1/008; A61H 1/006; A61H 1/0285; A61H 39/04; A61H 2201/1418; A61H 2201/1635; A61H 2201/165; A61H 2201/1695; A61H 2205/065; A61H 39/00; A61H 1/00; A61B 90/02; A61B 17/1322; A61B 17/1325; A61B 17/1327; A61G 13/12; A61G 13/1205; A61G 13/1235; A61G 13/124; A61G 13/1245; A61G 13/125

See application file for complete search history.

(56) References Cited

U.S. PATENT DOCUMENTS

| | | | | |
|---|---|---|---|---|
| 5,728,120 | A | 3/1998 | Shani et al. | |
| 2002/0151930 | A1* | 10/2002 | Mills | A61H 39/04 606/204 |
| 2003/0130690 | A1* | 7/2003 | Porrata | A61F 5/0118 606/204 |
| 2004/0210169 | A1* | 10/2004 | Hepburn | A61F 5/0118 601/40 |
| 2005/0049630 | A1* | 3/2005 | Ambach | A61B 17/1327 606/203 |

OTHER PUBLICATIONS

Extended European Search Report for related EP App No. 15824639.7 dated Aug. 20, 2018, 11 pgs.
Partial Supplementary European Search Report for EP App No. 15824639.7 dated Apr. 9, 2018, 12 pgs.

* cited by examiner

DEVICE FOR APPLYING PRESSURE TO BONES OF ARM AND METHOD OF TREATMENT

CROSS-REFERENCE TO RELATED APPLICATIONS

This application claims benefit of priority from Provisional U.S. Patent application Ser. No. 62/029,341, filed Jul. 25, 2014, the contents of which are incorporated by reference.

BACKGROUND

Field of Invention

The present invention relates generally to medical therapeutic systems, and deals more particularly with methods and devices for treating and managing functional disorders of the human carpus. More particularly, the present invention provides a splint for providing dynamic pressure to the transverse carpal, volar carpal, and intra-carpal ligaments, in a manner tending to relieve contractures of these ligaments and thus relieve the pain caused by the contractures of these ligaments.

Related Art

Carpal Tunnel Syndrome (CTS) may be a very debilitating affliction that can cause a great deal of pain and can in extreme cases render a hand and fingers to a useless state. CTS can occur when there is a constriction or an interference of the median nerve that passes through the carpal tunnel. This constriction of interference can cause numbness and/or tingling of the hand and/or fingers to varying degrees.

Some related art methods used for treatment (e.g., pain relief) of CTS include physical therapy, bracing, drug therapy, pain management (including injection therapy) and in extreme cases, surgery.

However, these related art methods may have various disadvantages and side effects. For example, the related art methods may result in high cost, drug addiction, and interference with use of the hands and fingers. Additionally, some of these methods may have diminishing effectiveness over time or iterative usage.

SUMMARY

An aspect of the present application may provide a method and/or an apparatus for treating CTS. Another aspect of the present application may provide a method and/or appliance directed to the relief of pressure on the median nerve. Another aspect may provide an appliance for the treatment of CTS which may be comfortable to the person wearing the appliance. Another aspect may provide an appliance for the treatment of CTS which may not unduly interfere with the normal activities of daily living.

Another aspect may provide an appliance which may be worn, adjusted, and removed by a patient with ordinary skill without adversely affecting the function of the appliance. Another aspect may provide an appliance which may be simple in construction.

Another aspect of the present application may allow treatment of carpal tunnel syndrome by using a device to provide lateral compression to the wrist to reduce the constriction of the median nerve and reduce interference thereon. By providing this lateral compression, the symptoms of the nerve compression may be reduced and the resulting numbness, tingling, pins and needle sensation and pain in the hands, forearm and thumb and fingers of the afflicted patient may be reduced, or even eliminated. This approach may also work equally well for ulnar nerve entrapment neuropathy at the level of the wrist by similarly relieving pressure on the Gyon's Canal at the level of the wrist. The principles for doing so may be the same as applied to relieve pressure for the carpal tunnel syndrome.

The subject matter of one aspect of the present application may include a device including: a flexible member having a first end and a second end; a linear member having a first end and a second end, the first end of the linear member being fixedly coupled to the first end of the flexible member and the second end of the linear member being slidingly coupled to the second end of flexible member; a cam pivotably coupled to the second end of the linear member, the cam contacting a surface of the second end of the flexible member; and a lever arm coupled to the cam. The lever arm may be movable between a first position in which the lever arm positions the cam to apply a first pressure to the surface of the second end of the flexible member, the first pressure being transmitted to the at least one bone of the human arm by the flexible member; and a second position in which the lever arm positions the cam to apply a second, larger pressure to the surface of the second end of the flexible member causing the second end of the flexible member to move relative to second end of the linear member and reduce a distance between the first end of the flexible member and the second end of the flexible member, the second, larger pressure being transmitted to the at least one bone of the human arm by the flexible member.

The subject matter of another aspect of the present application may include a device including: a first side arm having a first end and a second end; a second side arm having a first end and a second end, the first end of the second side arm being pivotably coupled to the first end of first side arm; a linear member having a first end and a second end, the first end of the linear member being connected to the second end of the first side arm, and the second end of the linear member slidingly connected to the second end of second side arm; and a cam pivotably coupled to the second end of the linear member, the cam contacting a the surface of the second end of the second side arm; and a lever arm coupled to the cam. The lever arm may be movable between: a first position in which the lever arm positions the cam member to apply a first pressure to the surface of the second end of second side arm, the first pressure being transmitted to the at least one bone of the human arm by at least one of the first side arm and the second side arm; and a second position in which the lever arm positions the cam member to apply a second, larger pressure to the surface of the second end of the second side arm and reduce a distance between the second end of the second side arm and the second end of the first side arm, the second, larger pressure being transmitted to the at least one bone of the human arm by at least one of the first side arm and the second side arm The subject matter of another aspect of the present application may include a method for relieving carpal tunnel syndrome of a person. The method may include placing a device around the wrist of the person. The device may include a pair of side arms, a linear member connecting the pair of side arms at one end, and a lever arm coupled to a cam attached to one of the pair of side arms. The method may also include articulating the lever arm to move the cam relative to one of the pair of side arms; applying, by the movement of the cam, a force to one or more of the pair of side arms; and applying, by the force applied to one or more of the pair of side arms, a pressure to at least one bone of the wrist of the person.

The subject matter of another aspect of the present application may include a method for relieving carpal tunnel syndrome of a person. The method may include placing a device around the wrist of the person. The device may include a flexible member having a first end and a second end, a linear member connecting the first end and second end of the flexible member, and a lever arm coupled to a cam attached to one of the first end and the second end of the flexible member. The method may also include: articulating the lever arm to move the cam relative to one of the first end and the second end of the flexible member; applying, by the movement of the cam, a force to one of the first end and the second end of the flexible member; and applying, by the force applied to one of the first end and the second end of the flexible member, a pressure to at least one bone of the wrist of the person.

Thus, example implementations of the present application may provide relief from symptoms of nerve compression resulting in numbness, tingling, pins and needle sensation and pain in the hands, forearm and thumb and fingers of the afflicted patient. Further example implementations of the present application may address the symptoms of carpal tunnel syndrome and ulnar nerve entrapment neuropathy at the level of the wrist through a new and unique approach. This approach may achieved by a mechanical device as illustrated in the attached FIGS. discussed below that may physically change and may lessen the pressure and interference exerted on the nerves passing through the carpel tunnel and Gyon's tunnel thereby eliminating the painful and debilitating symptoms of the condition. However, example implementations of the present application need not achieve this advantage, or any other advantage.

DETAILED DESCRIPTION

Figure 1:
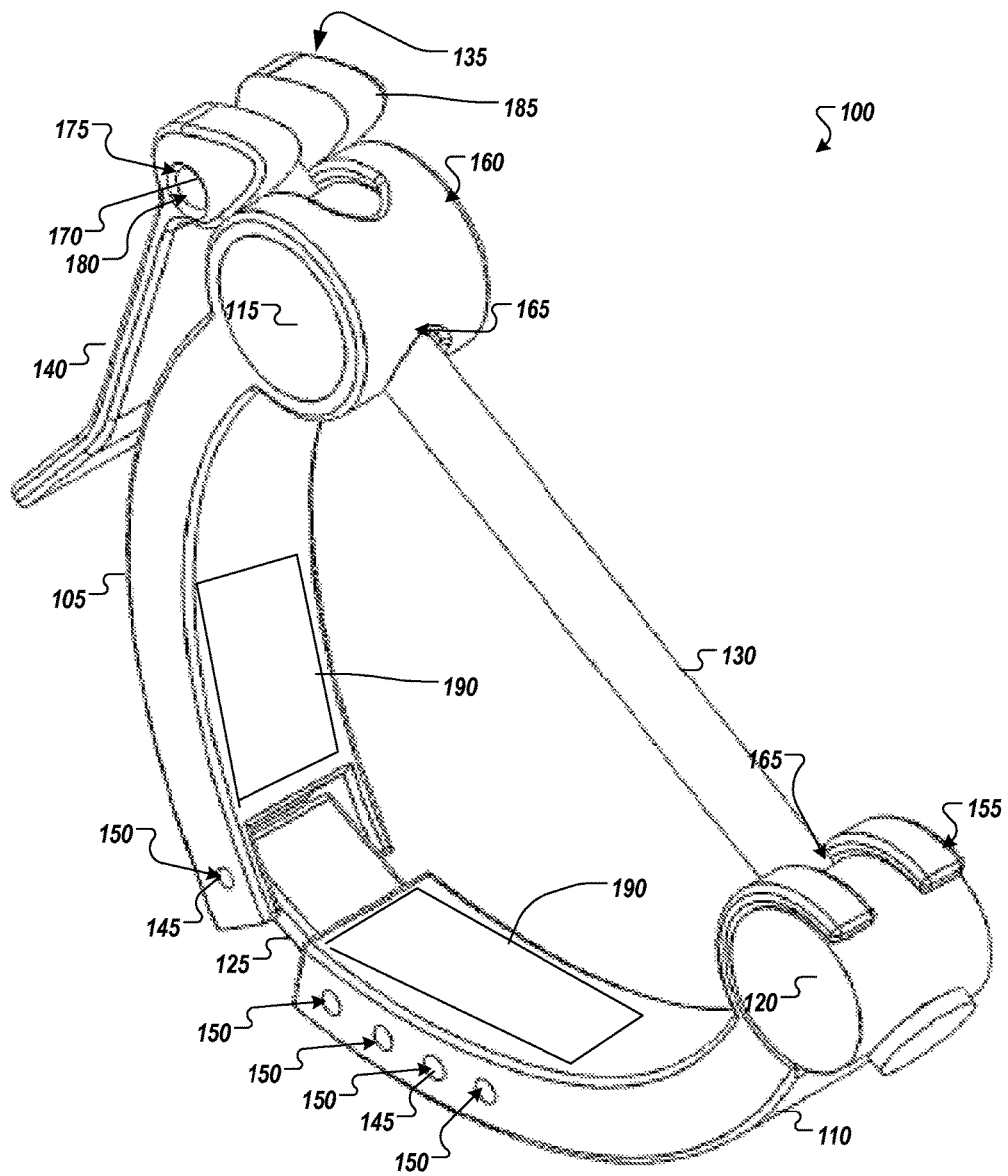
FIGS. 1 and 2 provide perspective views of a device according to one example implementation of a device according to the present application.
Figure 2:
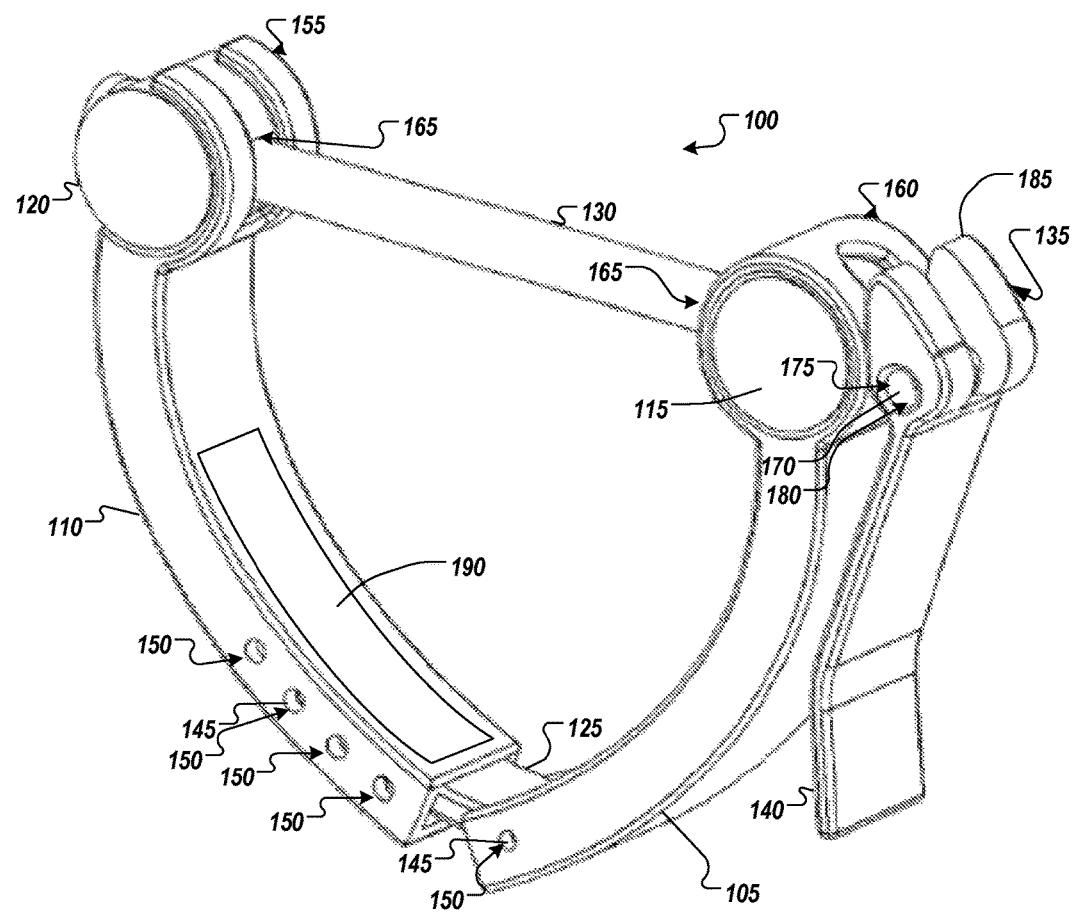
Figure 3:
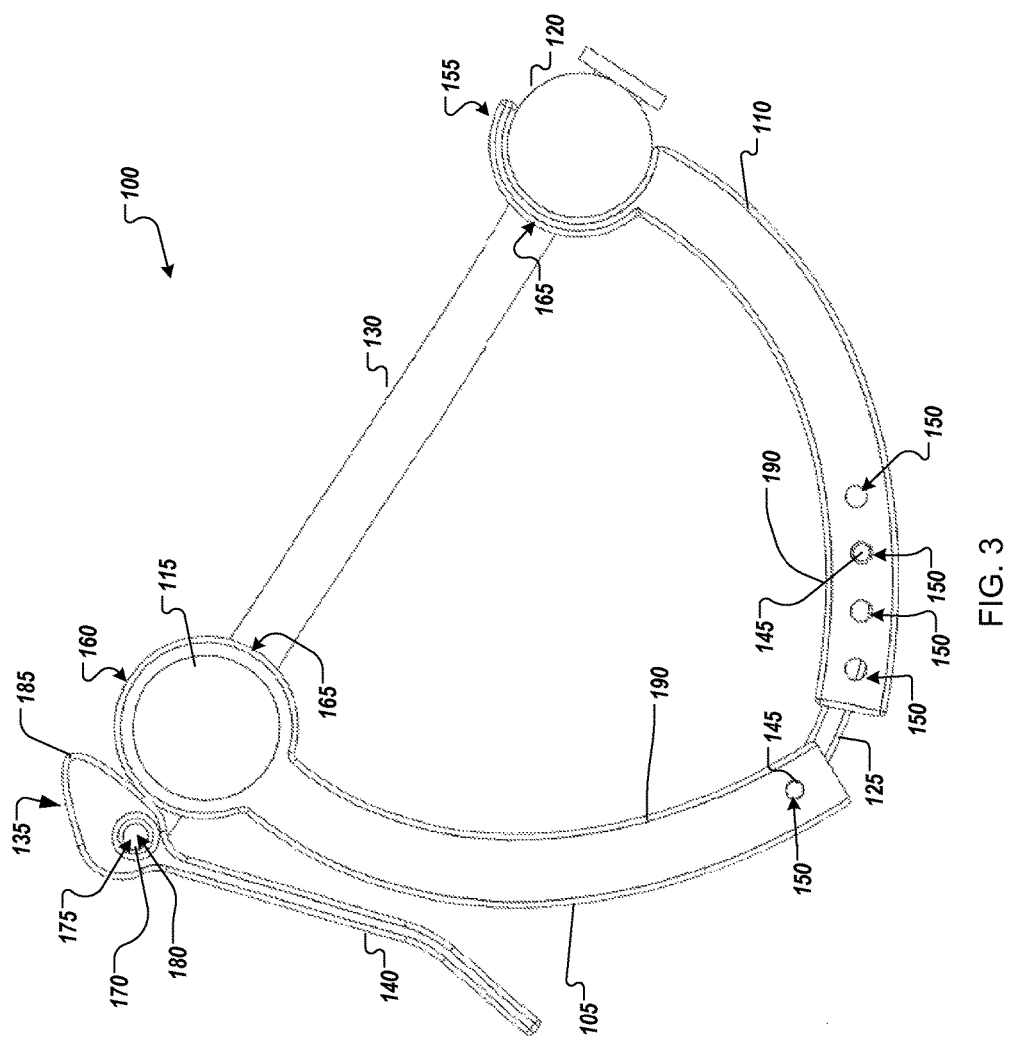
FIG. 3 provides a front view of the device of the example implementation of FIGS. 1 and 2.

FIGS. 1 and 2 provide perspective views of a device 100 according to one example implementation of a device according to the present application. FIG. 3 provides a front view of the device 100 of the example implementation of FIGS. 1 and 2. FIGS. 1-3 illustrate the device 100 according to an example implementation of the present application. The device 100 includes a pair of side arms 105,110, a pair of swivels 115,120, a connecting piece 125, a short bar 130, a cam 135 and a lever 140.

The pair of side arms 105,110 is joined together by the connecting piece 125 at one end of each of the side arms 105,100. The connecting piece 125 may be pivotally attached to each side arm 105,110, for example, using a spring loaded pin 145 inserted into one of a series of holes 150 formed on the end of each side arm 105,110. The specific hole of the series of holes 150 into which the spring loaded pin 145 is inserted on the end of each side arm 105,110, may be selected based on the size of a patient's wrist. Providing a series of holes may allow adjustment the device size to the size of the patient's wrist. As an alternative to the spring loaded pin 145 and holes 150, any other biasing structure may be substituted therefor, that performs the functions of joining side arms 105,110 to each other in a pivotably biased manner, as would be understood by those skilled in the art. Some alternative structures are illustrated in FIGS. 4-13 discussed below.

The respective top portions 155,160 of the arms 105,110 are each fitted to one of the pair of the swivels 115,120. Specifically, the top portion 155 of arm 110 may have a forked, semi-circular structure that receives the swivel 120 with the short bar 130 disposed within the fork. Further, the top portion 160 of the arm 105 may have circular enclosing structure that surrounds the swivel 115, but allows the short bar 130 to pass through. The structures of the swivels 115, 120 and the top portions 155,160 permit at least one end of the arms 105,110 (e.g., pivot about an axis at spring-loaded pin 145) to be movable as discussed in greater detail further below. Alternatively, only one of the arms 105,110 may be fitted to a swivel member 115,120, if the other arm 110,105 is stationary or formed integral with a short bar 130 as explained in greater detail further below.

In an alternative example implementation, the pair of arms 105,110 may be directly attached to one another without a connecting piece 125, such that the arms 105,110 pivot with respect to each other about a common pivot point (e.g., single unitary structure that is U-shaped or V-shaped). Accordingly, the size of the arms may vary to accommodate users of different sizes.

Each swivels 115,120 includes a hole 165 passing through it and is pivotably mounted to the respective side arm 105,110. Further, the holes 165 of the swivels 115,120 may each be aligned to receive the short bar 130 through the hole 165. As explained above, in an alternative example implementation, it is not necessary for swivels to be provided at both sides, and it is not necessary for the short bar 130 to be formed separately from the swivel 115,120. For example, one end of an arm 105,110 may be integrally formed with the short bar 130, while the other arm 110,105 is movably formed with the short bar 130 adjacent to the cam 135 and lever 140, which are discussed in greater detail below.

The short bar 130 may pass through the holes 165 of one or more swivels 115,120, and is connected to the cam 135 and the lever 140 at one end. The short bar 130 may be linear, curved, or otherwise shaped in any manner that provides a structure that permits a clamping function to applied to a user's wrist and other functions as disclosed herein with respect to the present example implementations. For example, if the end 155 of the arm 110 that is distant from the cam 135 and lever 140 may be integrally formed with the end of the short bar 130, then the short bar 130 may be curved or arc-shaped.

Further, the cam 135 and lever 140 may be provided to perform a function of providing pressure to the swivel 115 (or similarly structured element) so as to move (e.g., slide) the swivel 115 inward along the short bar 130 so as to move ends 155 and 160 closer to each other, and thus provide the necessary compression to the hand of the user at the wrist region, as further explained below. However, the present example implementations are not limited to the cam 135 and lever 140 structures, and other structures that perform the function of providing compression to the hand of the user at the wrist region may be substituted therefor without departing from the present inventive scope. For example, but not by way of limitation, instead of the cam 135 and lever 140 structures, another structure may be substituted therefor as would be understood in the art. For example, a handle or similar structure may be used that can be twisted, rotated, bent, or otherwise manipulated to perform the above-described function.

In the example implementation that uses the cam 135 and lever 140, the cam 135 and lever 140 is pivotally connected to the short bar 130 by a pin 170 (e.g., split pin) inserted through a hole 175 that is formed through the end of the short bar 130. This configuration may allow the cam 135 and lever 140 to pivot on an axis provided by the split pin 170. In other words, the spilt pin 170 may act as an axle firmly attached to the swivel 115 by a press fit into the swivel 115. The cam 135 and lever 140 may have a clearance hole 180 through which the split pin 170 may rotate. However, other structures performing these functions may be substituted therefor without departing from the scope of the example implementations.

As the lever arm 140 is moved about the axis of the split pin 170 (e.g. lifted) by the hand of a user, the lobe 185 of the cam 135 may contact a side (e.g., lateral side) of the swivel 115. As the lever arm 140 is further moved about the axis of the split pin 170, an increasing pressure may be exerted on the swivel 115 by the action of the cam lobe 185 and the increasing pressure on the swivel 115 may cause the side arm 105 to pivot. For example, the pivot may occur due to concentric movement on a spring pin 145 (or equivalent structure as would be understood by those skilled in the art) securing the side arms 105,110 to the connecting piece 125. Alternatively, the pivot may be directly between the two arms 105,110 without a connecting piece 125 or about a portion of a single arm 105,110, in the alternative example implementations explained above.

Further, the side arm 105 may pivot concentrically around the swivel 115 to allow the increasing pressure exerted by the cam 135 to further pull the short bar 130 through the clearance hole 165 of the swivel, thereby allowing the short bar 130 to exert tension on the opposing side arm 110.

The action of the lever arm 140, cam lobe 185, and short bar 130 may cause the distance between the side arms 105,110 to decrease as the cam 135 and lever 140 are moved. If this device 100 is circumferentially mounted around an arm or around a wrist-hand brace surrounding an arm, the device may exert bi-lateral inward pressure on the arm or brace, transferring pressure directly to the bones of the arm via the skin and muscle. Specifically, pressure may be transferred to the lower ends of the radius and ulna bones. This pressure may change the configuration of the carpal tunnel relieving the pressure on the median nerve passing through the carpel tunnel, thereby relieving the accompanying pain and numbness associated with CTS.

Example embodiments of the present application are not limited to the illustrated structure of the lever arm 140, cam 135, and short bar 130 and may have other structures that are capable of causing the distance between the side arms 105,110 to decrease in order to exert bi-lateral inward pressure on the arm or brace transferring pressure directly to the bones of the arm via the skin and muscle. For example, an over latch structure (e.g. a so-called "ski-boot buckle" latch) may replace the lever arm 140, cam 135, and short bar 130. The over latch structure could be used to connect the side arms 105,110 such that when the over latch structure is articulated by the hand of a user, the side arms 105,110 are brought more closely together to exert bi-lateral inward pressure on the arm or brace transferring pressure directly to the bones of the arm via the skin and muscle.

In some example implementations, one or more of the illustrated components may be formed may be formed using plastic such as nylon, delrin or any other hypoallergenic plastic. In some embodiments, the inherent flexibility and strength of these materials may permit the elimination of the swivels 115,120 while still providing a transfer of pressure to the lower ends of the radius and ulna bones. The device 100 may additionally, or alternatively, be injection molded to produce the parts necessary to manufacture a device 100 according to example implementations of the present application. Other materials or manufacturing techniques may be used as may be apparent to a person of ordinary skill in the art.

In order to circumferentially mount the device on an arm, one may disconnect the swivel 120 from the top portion 155 of the side arm 110 that is opposite the lever 140 and cam 135. This disconnecting may be achieved by extending the length of the side arm 110 and disengaging the swivel 120 from the top portion 155 of the side arm 110 opposite the lever 140 and cam 135. Alternatively, if there is an integral formation of the short bar 130 and the swivel 120 or related structure at an end 155 that is distant from the cam 135 and lever 140, the short bar may be shaped such that it is not necessary to disconnect and/or disengage the swivel 120 from the top portion 155 of the side arm 110.

In some example implementations, the short bar 130 and the swivel 120 may be removable from the top portion 155 of the side arm 110 opposite the lever 140 and cam 135. In some example implementations, the top portion 155 of the side arm 110 may not completely encircle the swivel 120 as illustrated, allowing removal and reattachment of the swivel 120 from the top portion 155 of the side arm 110 by moving the ends 155,160 of the side arms 105,110 towards each other and then moving the swivel 120 upward to disengage the swivel 120 from the top portion 155. In other example implementations, the top portion 160 of the side arm 105 may completely encircle the swivel 115 as illustrated. As explained above, side arm 105 and side arm 110 may be formed integrally with respect to each other, thus obviating the need for a connecting piece and spring pin, or the like. Further, side arm 110 may be formed integrally with the short bar, such that there is no swivel 120 at the connection of the side arm 110 and the end of the short bar 130. Additionally, the short bar 130 need not be linear. Further, if a structure different from the cam 135 and lever 140 is used (e.g., handle-like structure as explained above), then the swivel 115 may be modified, formed integrally with the side arm 105, or eliminated.

In some example implementations, the short bar 130 and the swivel 120 of the side arm 110 opposite from the lever 140 and cam 135 may be threaded. The threading of the short bar 130 and swivel 120 may allow the width of the device to be adjusted. For example, clockwise rotation of the cam 135 and lever 140 might allow the short bar 130 to thread into the swivel 120, thereby reducing the effective length of the short bar 130 and increasing the tension and/or pressure applied. This adjustment may enable initial pressure adjustment. Conversely, the cam 135 and lever 140 might be rotated counter-clockwise thereby lengthening the width of the distance between the side arms 105,110 allowing the removal of the swivel 120 from the mounting point on the side arm opposite the cam 135 and lever 140, allowing the device 100 to be installed circumferentially around the arm or installed around a brace installed on the arm. The directions of rotation may be reversed without departing from the inventive scope.

As an alternative to the above-described threaded structure of the short bar 130 and the swivel 120, other structures may be substituted therefor to provide size adjustability (e.g. size of the device 100 could be adjusted to the size of the user's wrist), as would be understood by those skilled in the art. Further, the device 100 may be made in different sizes (e.g., small, medium large), so as to eliminate or reduce the need for adjustable parts (such as the series of holes 150 and the threading of the short bar 130). In other words, the device may be sold or distributed in a plurality of fixed sizes, and a user or a prescribing medical professional (such as a nurse, doctor, physical therapist, etc.) may select the fixed size of the device rather than acquiring a device that is adjusted to the size of the user.

Further, in some example implementations, padding such as neoprene or other dermatologically inert foam may be provided to improve comfort and wear-ability of the device 100. For example, padding 190 may be placed on a portion or along the entire inner surfaces of the side arms 105,110 as illustrated. Padding may also be applied to the short bar 130 or any other component, which may contact or rub a user's skin, as may be apparent to a person of ordinary skill in the art.

Figure 4:
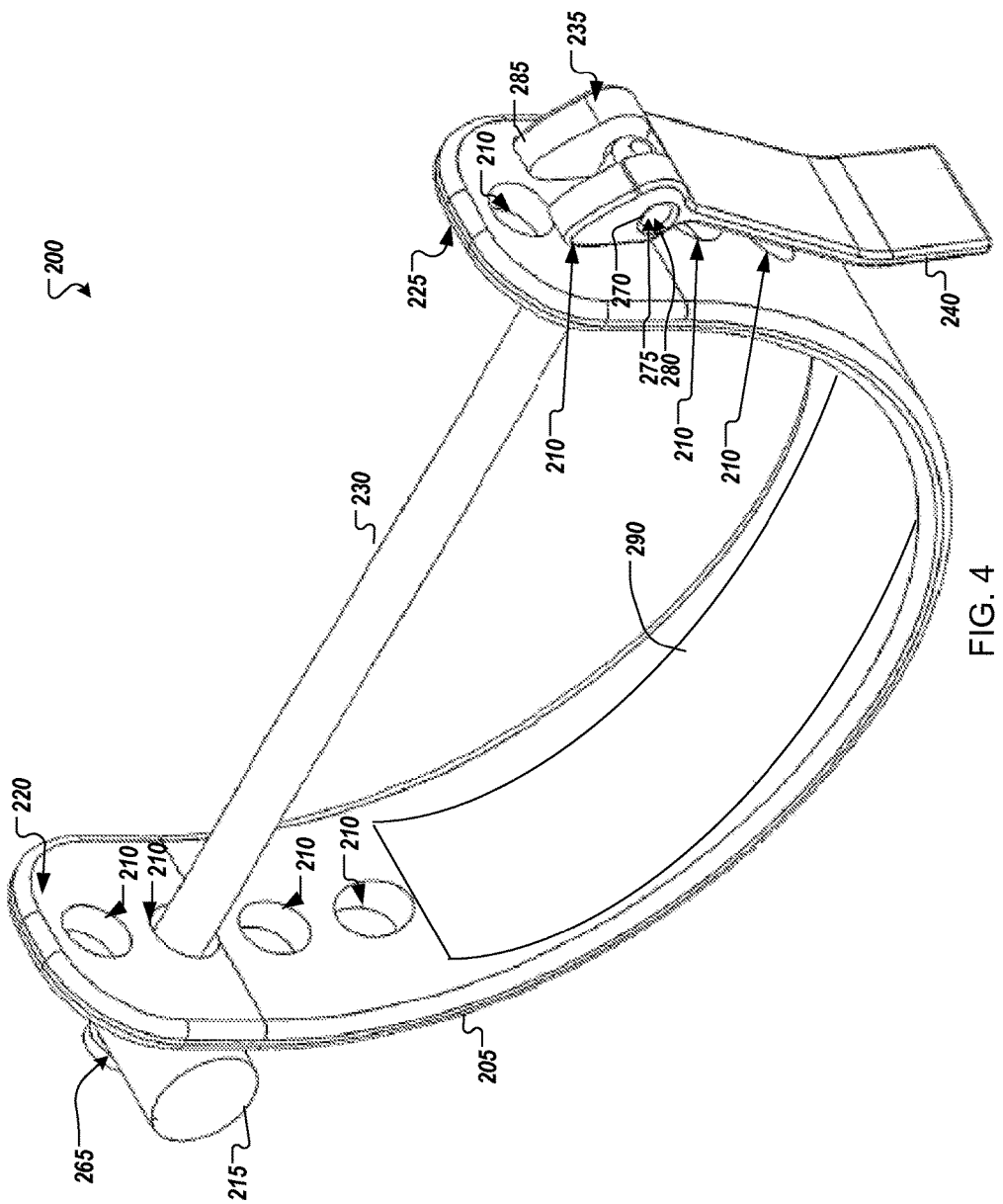
FIGS. 4 and 5 provide perspective views of a device according to another example implementation of the present application.
Figure 5:
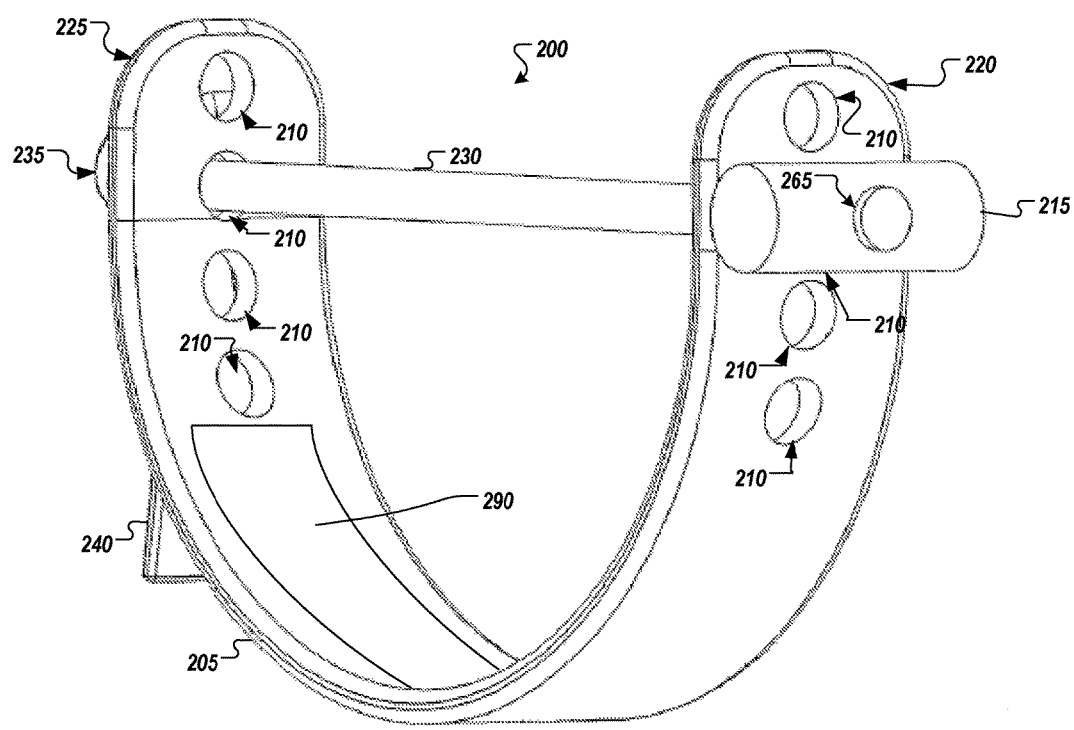
Figure 6:
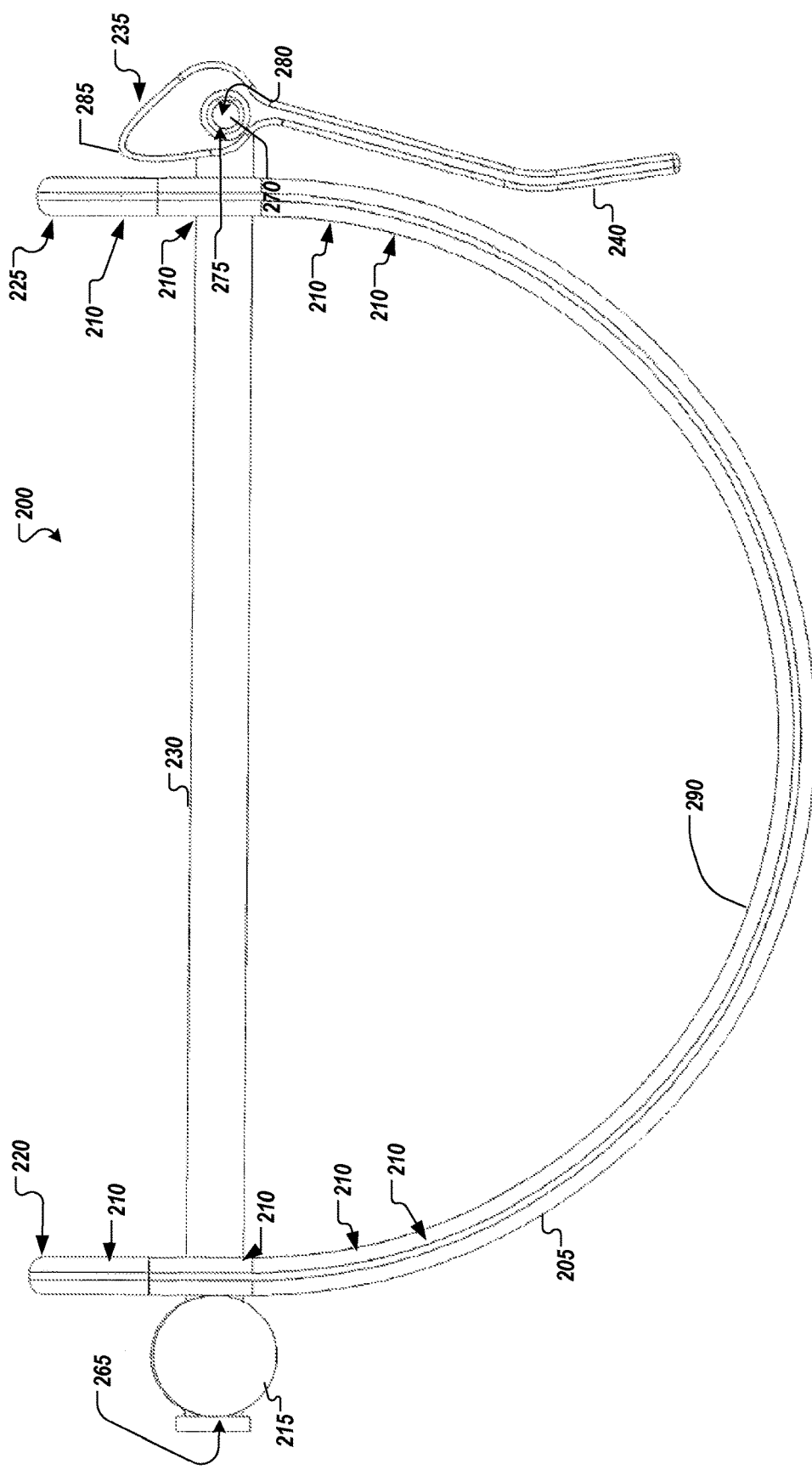
FIG. 6 provides a front view of the device of the example implementation of FIGS. 4 and 5.

FIGS. 4 and 5 provide perspective views of a device 200 according to another example implementation of the present application. FIG. 6 provides a front view of the device 200 of the example implementation of FIGS. 4 and 5. FIGS. 4-6 illustrate the device 200 according to another example implementation of the present application. Some aspects of this example implementation may be similar to the example implementation illustrate in FIGS. 1-3 discussed above. The device 200 includes a flexible member 205, a swivel 215, a short bar 230, a cam 235 and a lever 240.

The flexible member 205 includes a plurality of holes 210 at an end 220 of the flexible member 205 adjacent to the swivel 215. The flexible member 205 also includes a plurality of holes 210 at an end 225 of the flexible member 205 adjacent the cam 235 and lever 240. The short bar 230 is inserted through one of the holes 210 on each end 220,225 of the flexible member 205. The short bar 230 may be removed and reinserted through different holes 210 at one or both ends 220,225 to enable adjustment of size to a patient. In some embodiments, holes 210 may only be provided at one end 220,225 as discussed below.

The swivel 215 may include a hole 265 passing through the swivel 215 and be positioned outside of the flexible member 205. Further, the hole 265 of the swivel 215 may be aligned to receive the short bar 230 passing through the hole 265 formed through the swivel 215. The short bar 230 may pass through the hole 265 of the swivel 215, through the holes 210 at both ends of the flexible member 205 and be connected to the cam 235 and lever 240 at one end. The short bar 230 may be linear, curved, or otherwise shaped in any manner that provides a structure that permits a clamping function to be applied to a user's wrist and other functions as disclosed herein with respect to the present example implementations. For example, if the end 220 of the flexible member 205 that is distant from the cam 235 and lever 240 may be integrally formed with an end of the short bar 230, then the short bar 230 may be curved or arc-shaped.

Further, the cam 235 and lever 240 may be provided to perform a function of providing pressure to the end 225 of the flexible member 205 (or similarly structured element) so as to move (e.g., slide) the end 225 inward along the short bar 230 so as to move ends 220,225 closer to each other, and thus provide the necessary compression to the hand of the user at the wrist region, as further explained below. However, the present example implementations are not limited to the cam 235 and lever 240 structures, and other structures that perform the function of providing compression to the hand of the user at the wrist region may be substituted therefor without departing from the present inventive scope. For example, but not by way of limitation, instead of the cam 235 and lever 240 structures, another structure may be substituted therefor as would be understood in the art. For example, a handle or similar structure may be used that can be twisted, rotated, bent, or otherwise manipulated to perform the above-described function.

In the example implementation that uses the cam 235 and lever 240, the cam 235 and lever 240 is pivotally connected to the short bar 235 by a pin 270 (e.g., split pin) inserted through a hole 275 that is formed through the end of the short bar 230. This configuration may allow the cam 235 and lever 240 to pivot on an axis provided by the split pin 270. In other words, the split pin 270 may act as an axle firmly attached to an end of the short bar 230 by a press fit into the short bar 230. The cam 235 and lever 240 may have a clearance hole 280 through which the split pin 270 may rotate. However, other structures performing these functions may be substituted therefor without departing from the scope of the example implementations.

As the lever arm 240 is moved about the axis of the split pin 270 (e.g. lifted) by the hand of a user, the lobe 285 of the cam 235 may contact a side (e.g., lateral side) of the end 225 of the flexible member 205. As the lever arm 240 is further moved about the axis of the split pin 270, an increasing pressure may be exerted on the end 225 of the flexible member 205 by the action of the cam lobe 285 and the increasing pressure on the end 225 of the flexible member 205 may cause the ends 220,225 of the flexible member 205 to come together.

Further, the end 225 of the flexible member 205 may flex to allow the increasing pressure exerted by the cam 235 to further pull the short bar 230 through the hole 210 of the flexible member 205, thereby allowing the short bar 230 to exert tension on the other end 220 of the flexible member 205.

The action of the lever arm 240, cam lobe 285, and short bar 230 may cause the distance between the ends 220,225 of the flexible member 205 to decrease as the cam 235 and lever 240 are moved. If this device 200 is circumferentially mounted around an arm or around a wrist-hand brace surrounding an arm, the device 200 may exert bi-lateral inward pressure on the arm or brace transferring pressure directly to the bones of the arm via the skin and muscle. Specifically, pressure may be transferred to the lower ends of the radius and ulna bones. This pressure may change the configuration of the carpal tunnel relieving the pressure on the median nerve passing through the carpel tunnel, thereby relieving the accompanying pain and numbness associated with CTS.

Example embodiments of the present application are not limited to the illustrated structure of the lever arm 240, cam 235, and short bar 230 and may have other structures that are capable of causing the distance between the ends 220,225 of the flexible member 205 to decrease in order to exert bi-lateral inward pressure on the arm or brace transferring pressure directly to the bones of the arm via the skin and muscle. For example, an over latch structure (e.g. a so-called "ski-boot buckle" latch) may replace the lever arm 240, cam 235, and short bar 230. The over latch structure could be used to connect the ends 220,225 of the flexible member such that when the over latch structure is articulated by the hand of a user, the ends 220,225 of the flexible member 205 are brought more closely together to exert bi-lateral inward pressure on the arm or brace transferring pressure directly to the bones of the arm via the skin and muscle.

In some example implementations, one or more of the illustrated components may be formed may be formed using plastic such as nylon, delrin or any other hypoallergenic plastic. In some embodiments, the inherent flexibility and strength of these materials may permit the elimination of the swivel while still providing a transfer of pressure to the lower ends of the radius and ulna bones. The device 200 may additionally, or alternatively, be injection molded to produce the parts necessary to manufacture a device 200 according to example implementations of the present application. Other materials or manufacturing techniques may be used as may be apparent to a person of ordinary skill in the art.

In order to circumferentially mount the device on an arm, one may disconnect the cam 235 and lever 240 from the short bar 230 to remove from the end 225 of the flexible member 205. This disconnecting may be achieved by removing the pin 270 holding the short bar 230 to the cam 235 and lever 240 and sliding the short bar 230 through the hole 210 formed in the end 225 of the flexible member 205.

In some example implementations, the short bar 230 and the swivel 215 opposite from the lever 240 and cam 235 may be threaded. The threading of the short bar 230 and swivel 215 may allow the width of the device 200 to be adjusted. For example, clockwise rotation of the cam 235 and lever 240 might allow the short bar 230 to thread into the swivel 215, thereby reducing the effective length of the short bar 230 and increasing the tension and/or pressure applied. This adjustment may enable initial pressure adjustment. Conversely, the cam 235 and lever 240 might be rotated counter-clockwise thereby lengthening the width of the distance between the ends 220,225 of flexible member 205 allowing the removal of the swivel 215, allowing the device 200 to be installed circumferentially around the arm or installed around a brace installed on the arm. The directions of rotation may be reversed without departing from the inventive scope.

As an alternative to the above-described threaded structure of the short bar 230 and swivel 215, other structures may be substituted therefor to provide size adjustability (e.g. size of the device 200 could be adjusted to the size of the user's wrist), as would be understood by those skilled in the art. Further, the device 200 may be made in different sizes (e.g., small, medium large), so as to eliminate or reduce the need for adjustable parts (such as the series of holes 210 and the threading of the short bar 230). In other words, the device may be sold or distributed in a plurality of fixed sizes, and a user or a prescribing medical professional (such as a nurse, doctor, physical therapist, etc.) may select the fixed size of the device rather than acquiring a device that is adjusted to the size of the user.

Further, in some example implementations, padding such as neoprene or other dermatologically inert foam may be provided to improve comfort and wear-ability of the device 200. For example, padding 290 may be placed on a portion or along the entire inner surfaces of the flexible member 205 as illustrated. Padding may also be applied to the short bar 230 or any other component, which may contact or rub a user's skin, as may be apparent to a person of ordinary skill in the art.

Figure 7:
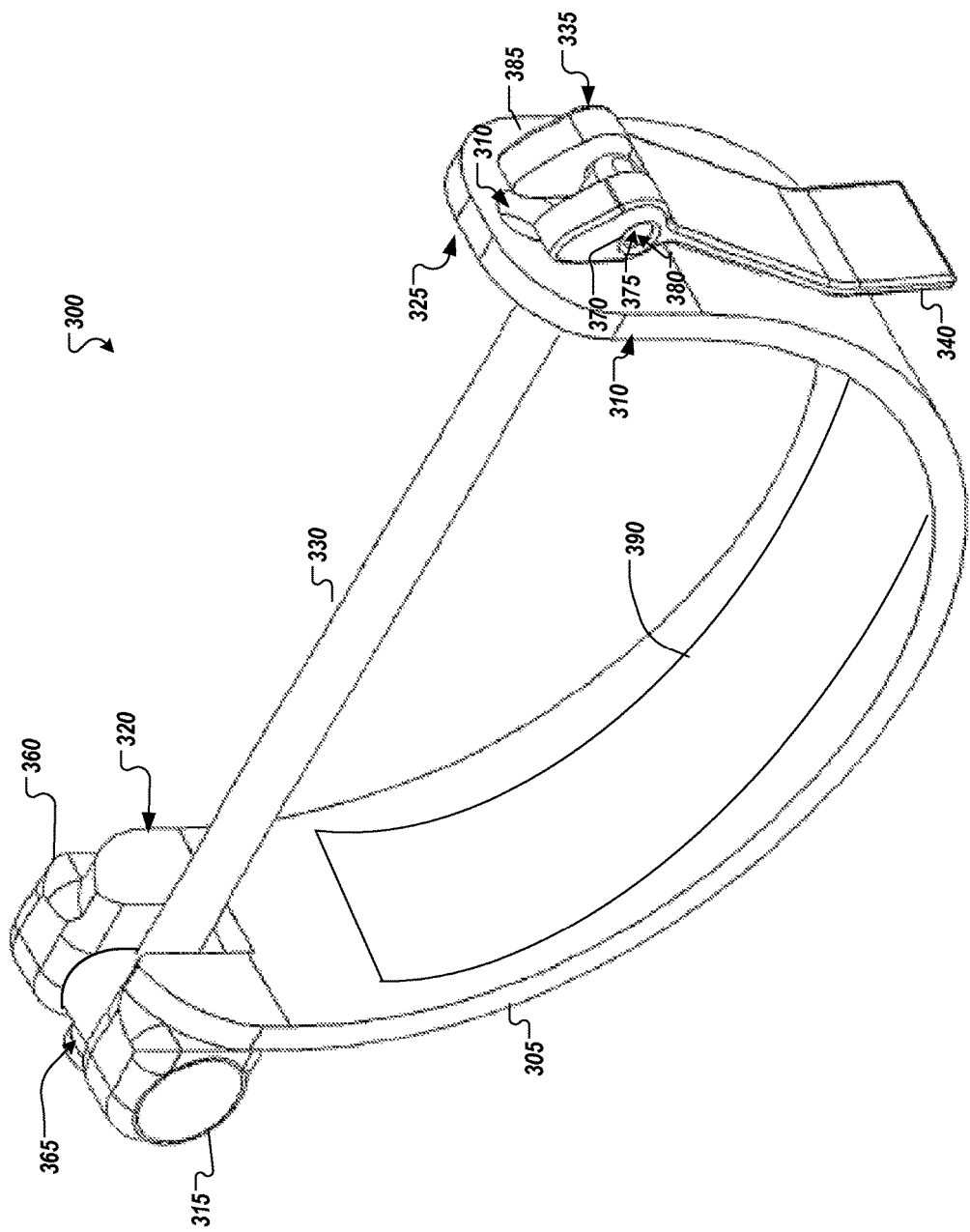
FIGS. 7 and 8 provide perspective views of a device according to another example implementation of the present application.
Figure 8:
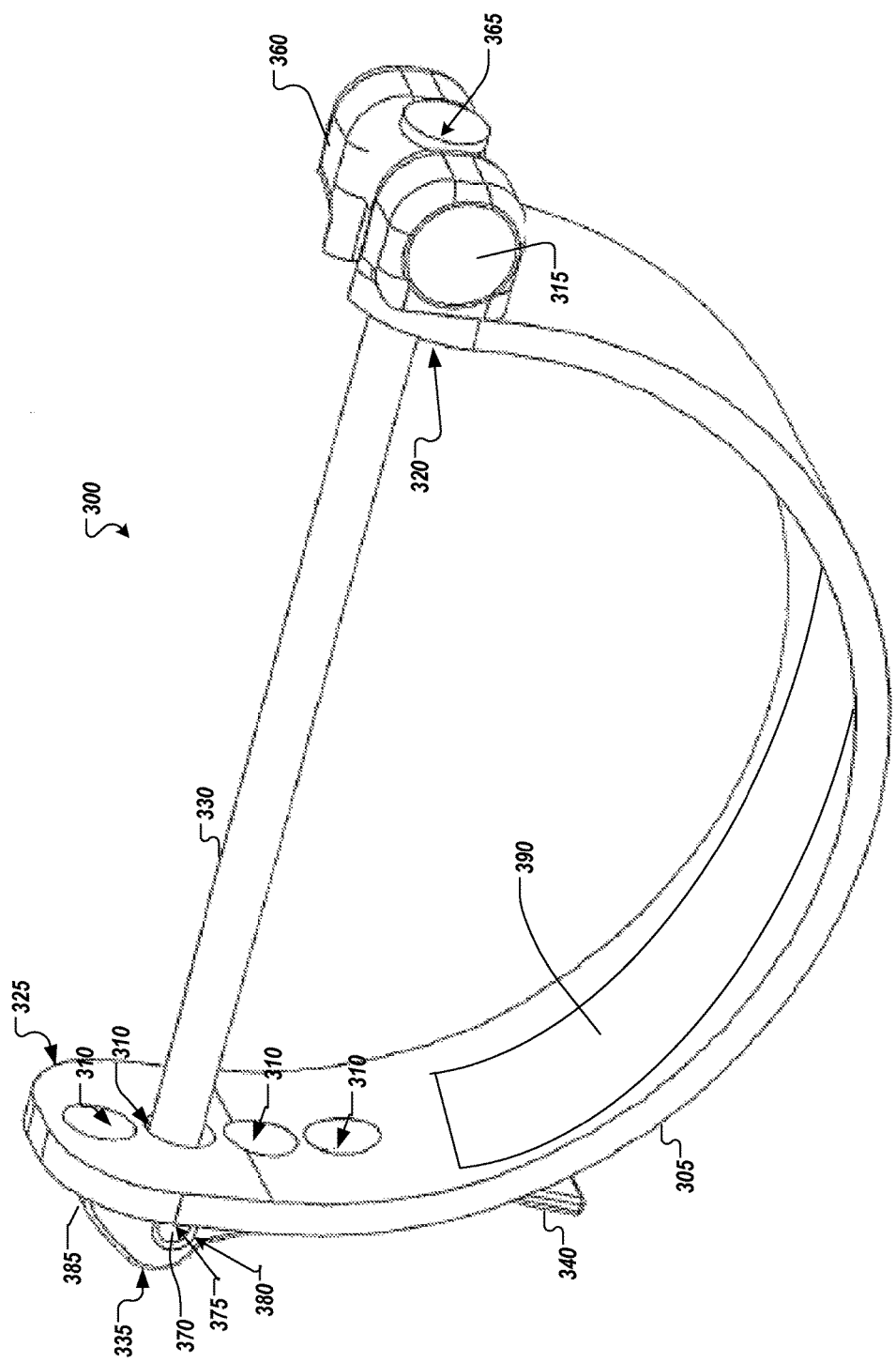
Figure 9:
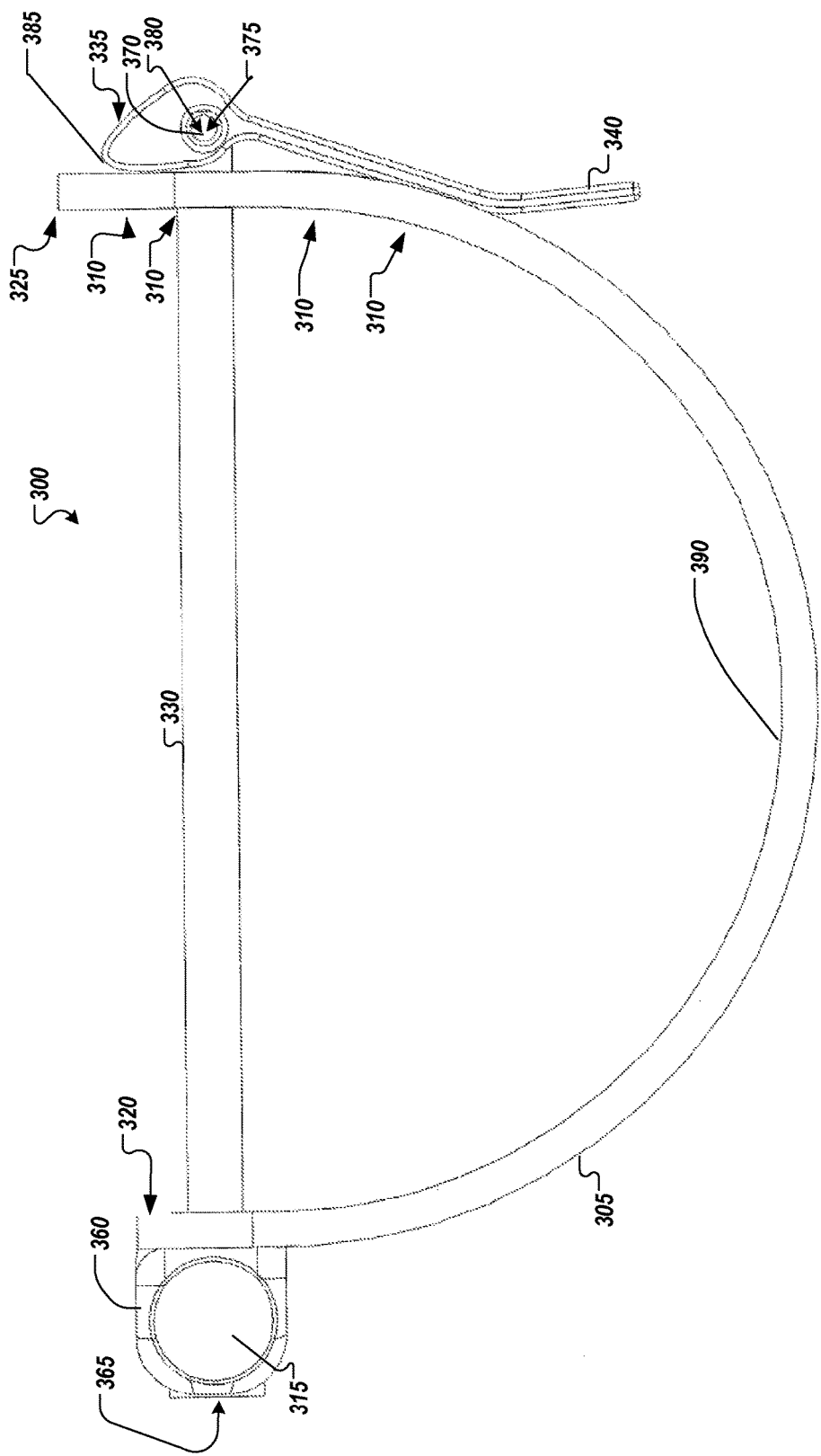
FIG. 9 provides a front view of the device of the example implementation of FIGS. 7 and 8.

FIGS. 7 and 8 provide perspective views of a device 300 according to another example implementation of the present application. FIG. 9 provides a front view of the device 300 of the example implementation of FIGS. 7 and 8. FIGS. 7-9 illustrate the device 300 according to another example implementation of the present application. Some aspects of this example implementation may be similar to the example implementation illustrated in FIGS. 1-6 discussed above. The device 300 includes a flexible member 305, a swivel 315, a short bar 330, a cam 335 and a lever 340.

At one end 320, the flexible member 305 includes a housing 360 configured to hold the swivel 315. The flexible member 305 also includes a plurality of holes 310 at an end 325 of the flexible member 305 adjacent the cam 335 and lever 340. The short bar 330 is inserted through one of the holes 310 on the end 325 of the flexible member 305. The short bar 330 may be removed and reinserted through different holes 310 at the end 325 to enable adjustment of size to a patient.

The swivel 315 may include a hole 365 passing through the swivel 315 and be positioned with the housing 360 integrally formed on the end 320 of the flexible member 305. Further, the hole 365 of the swivel 315 may be aligned to receive the short bar 330 passing through the hole 365 formed through the swivel 315. The short bar 330 may pass through the hole 365 of the swivel 315, through the housing 360 at one end 320 of the flexible member 305, through the hole 310 at the other end 325 of the flexible member 305 and be connected to the cam 335 and lever 340. The short bar 330 may be linear, curved, or otherwise shaped in any manner that provides a structure that permits a clamping function to be applied to a user's wrist and other functions as disclosed herein with respect to the present example implementations. For example, as the housing 360 integrally formed with the flexible member 305 may also be integrally formed with an end of the short bar 230, then the short bar 230 may be curved or arc-shaped.

Further, the cam 335 and lever 340 may be provided to perform a function of providing pressure to the end 325 of the flexible member 305 (or similarly structured element) so as to move (e.g., slide) the end 325 inward along the short bar 330 so as to move ends 220,225 closer to each other, and thus provide the necessary compression to the hand of the user at the wrist region, as further explained below. However, the present example implementations are not limited to the cam 335 and lever 340 structures, and other structures that perform the function of providing compression to the hand of the user at the wrist region may be substituted therefor without departing from the present inventive scope. For example, but not by way of limitation, instead of the cam 335 and lever 340 structures, another structure may be substituted therefor as would be understood in the art. For example, a handle or similar structure may be used that can be twisted, rotated, bent, or otherwise manipulated to perform the above-described function.

In the example implementation that uses the cam 335 and lever 340, the cam 335 and lever 340 is pivotally connected to the short bar 335 by a pin 370 (e.g., split pin) inserted through a hole 375 that is formed through the end of the short bar 330. This configuration may allow the cam 335 and lever 340 to pivot on an axis provided by the split pin 370.

In other words, the split pin 370 may act as an axle firmly attached to an end of the short bar 330 by a press fit into the short bar 330. The cam 335 and lever 340 may have a clearance hole 380 through which the split pin 370 may rotate. However, other structures performing these functions may be substituted therefor without departing from the scope of the example implementations.

As the lever arm 340 is moved about the axis of the split pin 370 (e.g. lifted) by the hand of a user, the lobe 385 of the cam 335 may contact a side (e.g., lateral side) of the end 325 of the flexible member 305. As the lever arm 340 is further moved about the axis of the split pin 270, an increasing pressure may be exerted on the end 325 of the flexible member 305 by the action of the cam lobe 385 and the increasing pressure on the end 325 of the flexible member 305 may cause the ends 320,325 of the flexible member 305 to come together.

Further, the end 325 of the flexible member 305 may flex to allow the increasing pressure exerted by the cam 335 to further pull the short bar 330 through the hole 310 of the flexible member 305, thereby allowing the short bar 330 to exert tension on the other end 320 of the flexible member 305.

The action of the lever arm 340, cam lobe 385, and short bar 330 may cause the distance between the ends 320,325 of the flexible member 305 to decrease as the cam 335 and lever 340 are moved. If this device 300 is circumferentially mounted around an arm or around a wrist-hand brace surrounding an arm, the device 300 may exert bi-lateral inward pressure on the arm or brace transferring pressure directly to the bones of the arm via the skin and muscle. Specifically, pressure may be transferred to the lower ends of the radius and ulna bones. This pressure may change the configuration of the carpal tunnel relieving the pressure on the median nerve passing through the carpel tunnel, thereby relieving the accompanying pain and numbness associated with CTS.

Example embodiments of the present application are not limited to the illustrated structure of the lever arm 340, cam 335, and short bar 330 and may have other structures that are capable of causing the distance between the ends 320,325 of the flexible member 305 to decrease in order to exert bi-lateral inward pressure on the arm or brace transferring pressure directly to the bones of the arm via the skin and muscle. For example, an over latch structure (e.g. a so-called "ski-boot buckle" latch) may replace the lever arm 340, cam 335, and short bar 330. The over latch structure could be used to connect the ends 320, 325 of the flexible member such that when the over latch structure is articulated by the hand of a user, the ends 320,325 of the flexible member 305 are brought more closely together to exert bi-lateral inward pressure on the arm or brace transferring pressure directly to the bones of the arm via the skin and muscle.

In some example implementations, one or more of the illustrated components may be formed may be formed using plastic such as nylon, delrin or any other hypoallergenic plastic. In some embodiments, the inherent flexibility and strength of these materials may permit the elimination of the swivel 315 while still providing a transfer of pressure to the lower ends of the radius and ulna bones. The device 300 may additionally, or alternatively, be injection molded to produce the parts necessary to manufacture a device 300 according to example implementations of the present application. Other materials or manufacturing techniques may be used as may be apparent to a person of ordinary skill in the art.

In order to circumferentially mount the device on an arm, one may disconnect the cam 335 and lever 340 from the short bar 330 to remove from the end 325 of the flexible member 305. This disconnecting may be achieved by removing the pin 370 holding the short bar 330 to the cam 335 and lever 340 and sliding the short bar 330 through the hole 310 formed in the end 325 of the flexible member 305.

In some example implementations, the short bar 330 and the swivel 315 opposite from the lever 340 and cam 335 may be threaded. The threading of the short bar 330 and swivel 315 may allow the width of the device 300 to be adjusted. For example, clockwise rotation of the cam 335 and lever 340 might allow the short bar 330 to thread into the swivel 315, thereby reducing the effective length of the short bar 330 and increasing the tension and/or pressure applied. This adjustment may enable initial pressure adjustment. Conversely, the cam 335 and lever 340 might be rotated counterclockwise thereby lengthening the width of the distance between the ends 320,325 of flexible member 305 allowing the removal of the swivel 315, allowing the device 300 to be installed circumferentially around the arm or installed around a brace installed on the arm. The directions of rotation may be reversed without departing from the inventive scope.

As an alternative to the above-described threaded structure of the short bar 330 and swivel 315, other structures may be substituted therefor to provide size adjustability (e.g. size of the device 300 could be adjusted to the size of the user's wrist), as would be understood by those skilled in the art. Further, the device 300 may be made in different sizes (e.g., small, medium large), so as to eliminate or reduce the need for adjustable parts (such as the series of holes 310 and the threading of the short bar 330). In other words, the device may be sold or distributed in a plurality of fixed sizes, and a user or a prescribing medical professional (such as a nurse, doctor, physical therapist, etc.) may select the fixed size of the device rather than acquiring a device that is adjusted to the size of the user.

Further, in some example implementations, padding such as neoprene or other dermatologically inert foam may be provided to improve comfort and wear-ability of the device 300. For example, padding 390 may be placed on a portion or along the entire inner surfaces of the flexible member 305 as illustrated. Padding may also be applied to the short bar 330 or any other component, which may contact or rub a user's skin, as may be apparent to a person of ordinary skill in the art.

Figure 10:
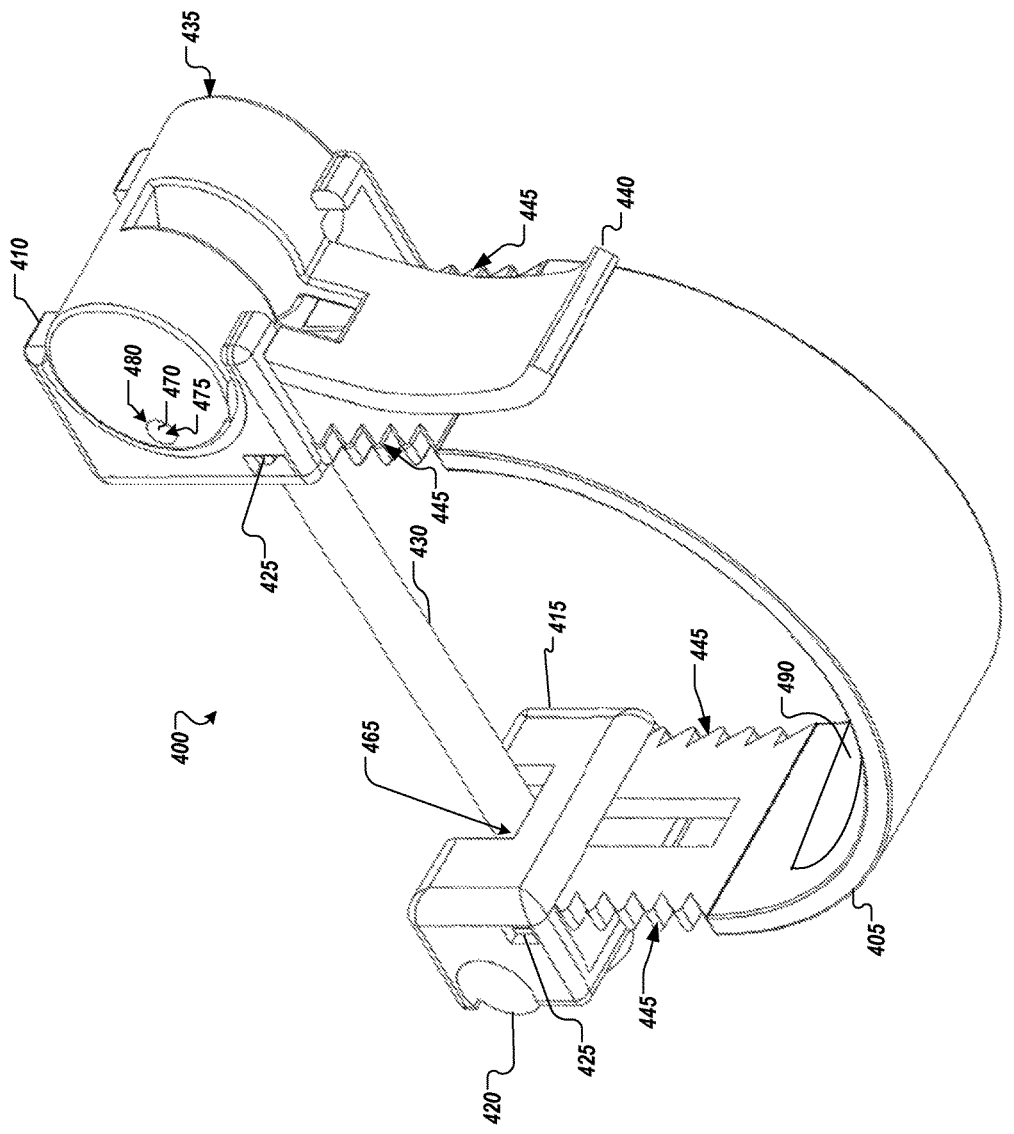
FIGS. 10 and 11 provide perspective views of a device according to another example implementation of the present application.
Figure 11:
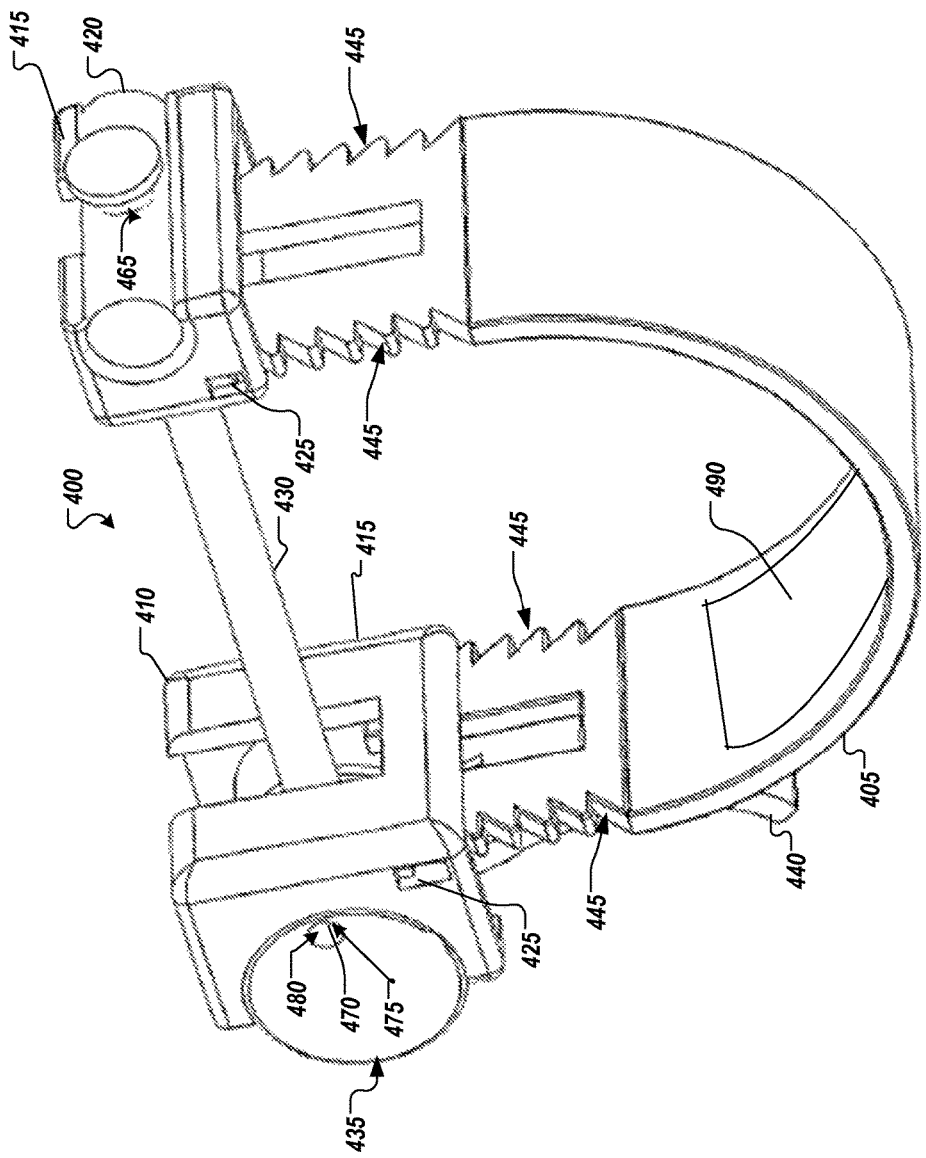
Figure 12:
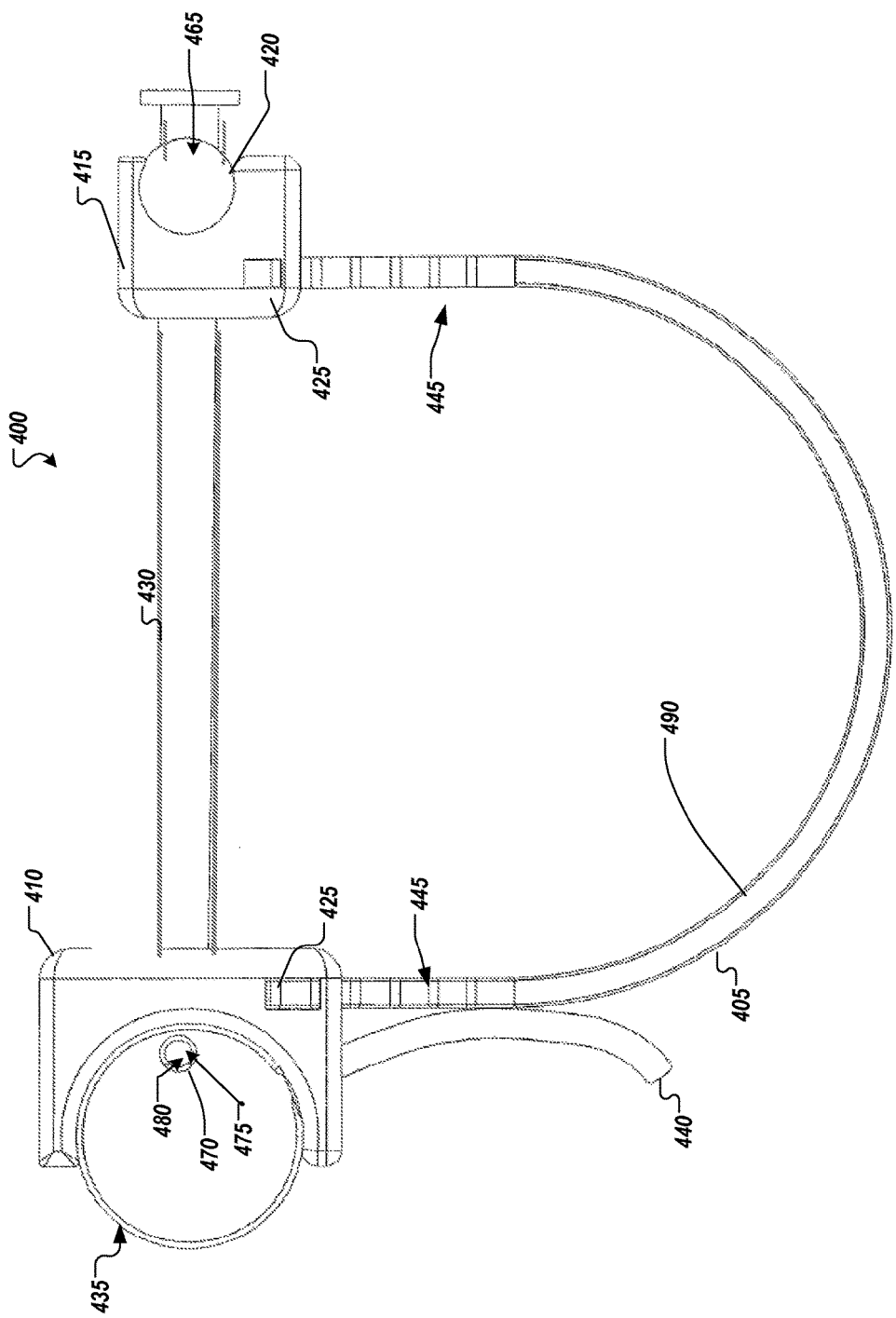
FIG. 12 provides a front view of the device of the example implementation of FIGS. 10 and 11.
Figure 13:
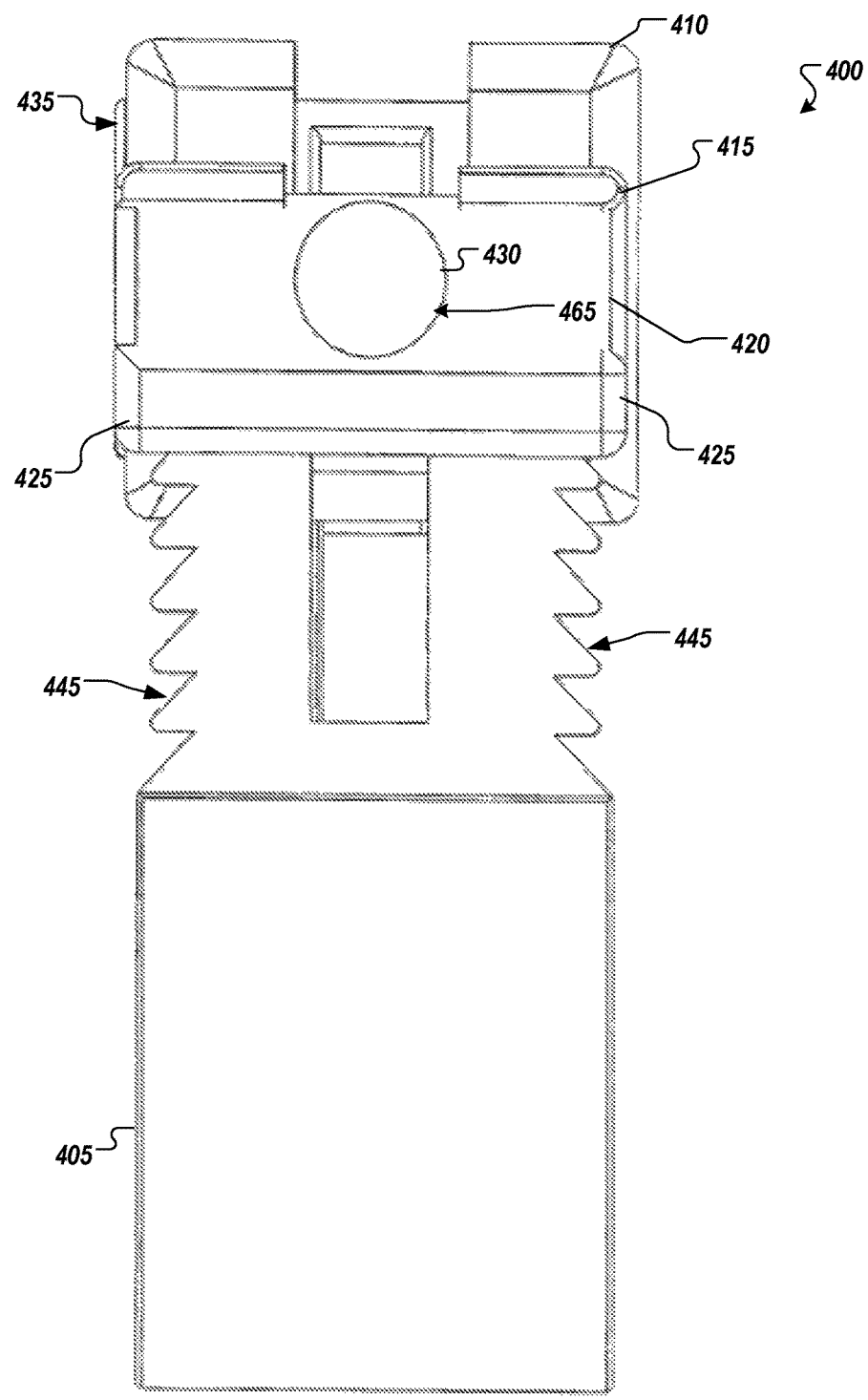
FIG. 13 provides an end view of the device of the example implementation of FIGS. 10 and 11.

FIGS. 10 and 11 provide perspective views of a device 400 according to another example implementation of the present application. FIG. 12 provides a front view of the device 400 of the example implementation of FIGS. 10 and 11. FIG. 13 provides an end view of the device 400 of the example implementation of FIGS. 10 and 11. FIGS. 10-13 illustrate the device 400 according to another example implementation of the present application. The device 400 includes a flexible member 405, a pair of upper blocks 410,415, a swivel 420, a short bar 430, a cam 435 and a lever 440.

The flexible member 405 is joined to each of the upper blocks 410, 415 at both ends of the flexible member 405 by an adjustment relief mechanism 425 of each side. The adjustment relief mechanism 425 may include a flexible notch that engages serrated portions 445 formed on each end of the flexible member 405. By changing the depth of insertion of the serrated portion 445 into the adjustment relief mechanism 425 on one or both upper blocks 410,415 may enable adjustment of size of the device 400 to a patient. In some example implementations, the adjustment relief mechanism 425 and serrated portion 445 may only be provided on one side of the flexible member 405 or any other equivalent adjustment structure that allows for adjustment of the size of the device 400 may be substituted therefor, as would be understood by those skilled in the art.

On one side of the device 300, the swivel 420 may be fitted into one of the upper blocks 415 joined to an end of the flexible member 405. Specifically, the upper block 415 may have a forked, semi-circular structure that receives the swivel 420 with the short bar 430 disposed within the fork. On the other end of the flexible member 405 of the device 300, the upper block 410 may have a forked, semi-circular structure that receives the cam 435 with the short bar 430 disposed within the fork. The structures of the upper blocks 410,415 permit at least one end of the flexible member 405 to be movable relative to the other end of the flexible member 405 as discussed in greater detail further below.

The swivel 420 includes a hole 465 passing through it and is pivotably mounted to the upper block 415. Further, the hole 465 of the swivel 420 may be aligned to receive the short bar 430 through the hole 465. As discussed above, in an alternative example implementation, swivels may be provided on both sides, and it is not necessary for the short bar 130 to be formed separately from the swivel 420. For example, one upper block 410,415 may be integrally formed with the short bar 430, while the other upper block 415,410 is movably formed with the short bar 430 adjacent to the cam 435 and lever 440.

The short bar 130 may pass through the holes 465 of the swivel 420 at one end and be connected to the cam 435 and the lever 440 at the other, opposite end. The short bar 430 may be linear, curved, or otherwise shaped in any manner that provides a structure that permits a clamping function to be applied to a user's wrist and other functions as disclosed herein with respect to the present example implementations. For example, if the upper housing 415 that is distant from the cam 435 and lever 440 may be integrally formed with the end of the short bar 430, then the short bar 430 may be curved or arc-shaped.

Further, the cam 435 and lever 440 may be provided to perform a function of providing pressure to the upper block 410 (or similarly structured element) so as to move (e.g., slide) the upper block 410 inward along the short bar 430 so as to move the upper blocks 410 and 415 closer to each other, and thus provide the necessary compression to the hand of the user at the wrist region, as further explained below. However, the present example implementations are not limited to the cam 435 and lever 440 structures, and other structures that perform the function of providing compression to the hand of the user at the wrist region may be substituted therefor without departing from the present inventive scope. For example, but not by way of limitation, instead of the cam 435 and lever 440 structures, another structure may be substituted therefor as would be understood in the art. For example, a handle or similar structure may be used that can be twisted, rotated, bent, or otherwise manipulated to perform the above-described function.

In the example implementation that uses the cam 435 and lever 440, the cam 435 and lever 440 is pivotally connected to the short bar 430 by a pin 470 (e.g., split pin) inserted through a hole 475 that is formed through the end of the short bar 430. Further, the cam 435 and lever 440 may have a clearance hole 480. In some example implementations, the clearance hole 480 may be offset from a center of the cam 435, such that pivoting the lever 440 causes the cam 435 to rotate relative to the upper block 410 and the relative rotation of causes the clearance hole 480 (and the pin 470) to move relative to the upper block 410. However, other structures performing these functions may be substituted therefor without departing from the scope of the example implementations.

As the lever arm 440 is moved upward (e.g. lifted) by the hand of a user, the relative movement between clearance hole 480 (and the pin 470) and the upper block 410 causes a shortening of the relative length of the short bar 430. As the lever arm 440 is further moved upward, an increased tension may be exerted on the upper block 410 causing the upper blocks 410,415 to be pulled together causing the ends of the flexible member 405 to come together.

Further, the action of the lever 440 and the movement of the clearance hole 480 (and the pin 470) relative to the upper block 410 may further pull the short bar 430 through the upper block 410, thereby allowing the short bar 130 to exert tension on the opposing upper block 415.

The action of the lever arm 440, cam 435 and short bar 530 may cause the distance between the upper blocks 410,415 (and the ends of the flexible member 405 attached thereto) to decrease as the cam 435 and lever 440 are moved. If this device 400 is circumferentially mounted around an arm or around a wrist-hand brace surrounding an arm, the device may exert bi-lateral inward pressure on the arm or brace transferring pressure directly to the bones of the arm via the skin and muscle. Specifically, pressure may be transferred to the lower ends of the radius and ulna bones. This pressure may change the configuration of the carpal tunnel relieving the pressure on the median nerve passing through the carpel tunnel, thereby relieving the accompanying pain and numbness associated with CTS.

Example embodiments of the present application are not limited to the illustrated structure of the lever arm 440, cam 435, and short bar 430 and may have other structures that are capable of causing the distance between the upper blocks 410,415 (and the ends of the flexible member 405 attached thereto) to decrease in order to exert bi-lateral inward pressure on the arm or brace transferring pressure directly to the bones of the arm via the skin and muscle. For example, an over latch structure (e.g. a so-called "ski-boot buckle" latch) may replace the lever arm 440, cam 435, and short bar 430. The over latch structure could be used to connect the upper blocks 410,415 (and the ends of the flexible member 405 attached thereto) such that when the over latch structure is articulated by the hand of a user, the upper blocks 410,415 (and the ends of the flexible member 405 attached thereto) are brought more closely together to exert bi-lateral inward pressure on the arm or brace transferring pressure directly to the bones of the arm via the skin and muscle.

In some example implementations, one or more of the illustrated components may be formed may be formed using plastic such as nylon, delrin or any other hypoallergenic plastic. In some embodiments, the inherent flexibility and strength of these materials may permit the elimination of the swivel 420 while still providing a transfer of pressure to the lower ends of the radius and ulna bones. The device 400 may additionally, or alternatively, be injection molded to produce the parts necessary to manufacture a device 400 according to example implementations of the present application. Other materials or manufacturing techniques may be used as may be apparent to a person of ordinary skill in the art.

In order to circumferentially mount the device on an arm, one may disconnect the swivel 420 from the upper block 415 that is opposite the lever 440 and cam 435. This disconnecting may be achieved by disengaging the swivel 420 from the upper block 415 opposite the lever 440 and cam 435. Alternatively, if there is an integral formation of the short bar 430 and the swivel 420 or related structure at an end of the flexible member that is distant from the cam 435 and lever 440, the short bar 430 may be shaped such that it is not necessary to disconnect and/or disengage the swivel 420 from the upper block 415.

In some example implementations, the short bar 430 and the swivel 420 may be removable from the upper block 415 opposite the lever 440 and cam 435. In some example implementations, the upper block 415 may not completely encircle the swivel 420, allowing removal and reattachment as illustrated. In other example implementations, the upper block 415 may completely encircle the swivel 420 as illustrated, allowing removal and reattachment of the swivel 420 from the upper block 415 by moving the upper blocks 410,415 towards each other and then moving the swivel 420 upward to disengage the swivel 420 from the upper block 415. The upper blocks 410,415 may be formed integrally with the flexible member 405 obviating the need for one or more of the serrated portions 445. Further, the upper blocks 410,415 may also or alternatively be formed integrally with the short bar 430, such that there is no swivel 420 at the connection of the upper block 415 and the end of the short bar 430. Additionally, the short bar 430 need not be linear.

In some example implementations, the short bar 430 and the swivel 420 of the upper block 415 opposite from the lever 440 and cam 435 may be threaded. The threading of the short bar 430 and swivel 420 may allow the width of the device 400 to be adjusted. For example, clockwise rotation of the cam 435 and lever 440 might allow the short bar 430 to thread into the swivel 420, thereby reducing the effective length of the short bar 430 and increasing the tension and/or pressure applied. This adjustment may enable initial pressure adjustment. Conversely, the cam 435 and lever 440 might be rotated counter-clockwise thereby lengthening the width of the distance between the upper blocks 410, 415 allowing the removal of the swivel 420 from the upper block 415 opposite the cam 435 and lever 440, allowing the device 400 to be installed circumferentially around the arm or installed around a brace installed on the arm. The directions of rotation may be reversed without departing from the inventive scope.

As an alternative to the above-described threaded structure of the short bar 430 and the swivel 420, other structures may be substituted therefor to provide size adjustability (e.g. size of the device 400 could be adjusted to the size of the user's wrist), as would be understood by those skilled in the art. Further, the device 400 may be made in different sizes (e.g., small, medium large), so as to eliminate or reduce the need for adjustable parts (such as the serrated portions 445, the relief adjustment mechanism 425 and the threading of the short bar 130). In other words, the device may be sold or distributed in a plurality of fixed sizes, and a user or a prescribing medical professional (such as a nurse, doctor, physical therapist, etc.) may select the fixed size of the device rather than acquiring a device that is adjusted to the size of the user.

Further, in some example implementations, padding such as neoprene or other dermatologically inert foam may be provided to improve comfort and wear-ability of the device 400. For example, padding 490 may be placed on a portion or along the entire inner flexible member 405 as illustrated. Padding may also be applied to the short bar 430 or any other component, which may contact or rub a user's skin, as may be apparent to a person of ordinary skill in the art.

Figure 14:
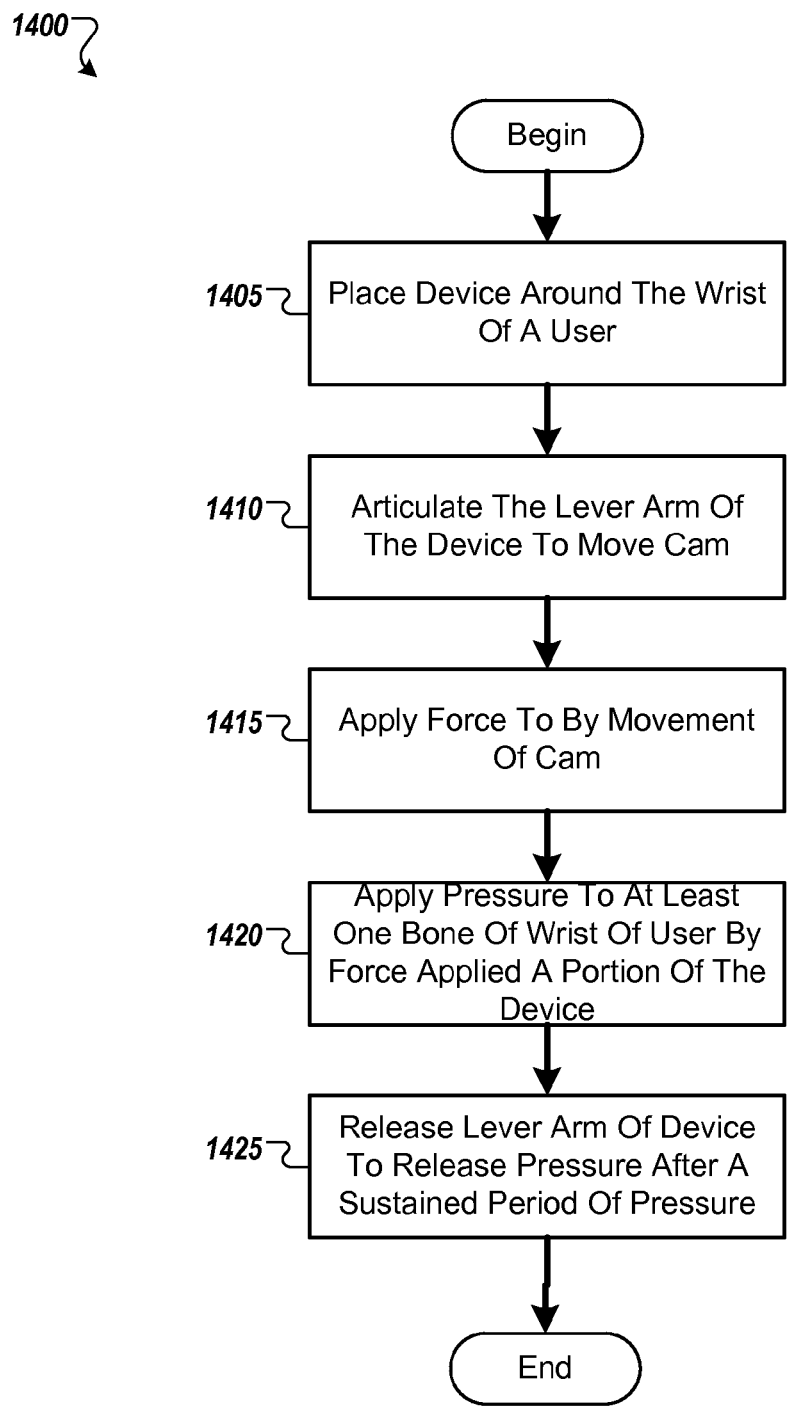
FIG. 14 provides a process flow of a treatment process according to an example implementation of the present application.

FIG. 14 provides a process flow of a treatment process 1400 according to an example implementation of the present application. In process 1400, a device is wrapped around a user or patient's wrist in 1405. The device may be a device according to an example implementation of the present application. For example, device 100 of FIGS. 1-3, device 200 of FIGS. 4-6, device 300 of FIGS. 7-9, or device 400 of FIGS. 10-14 may be used. The device may be wrapped around the user or patient's wrist may be installed by separating the short bar (130,230,330,430) from the flexible member (205,305,405) or one of the side arms (105,110) as discussed above. In some embodiments, the device may be wrapped around the user or patient's wrist such that the short bar (130,230,330,430) is extends across the inside of the user or patient's wrist. In other embodiments, the device may be wrapped around the user or patient's wrist such that the short bar (130,230,330,430) is extends across the outside of the user or patient's wrist.

Once the device (100,200,300,400) has been placed around the user's wrist, the lever arm (140,240,340,440) is articulated to move the cam (135,235,335,435) in 1410. The lever arm (140,240,340,440) may be articulated by the user, a medical professional (such as a nurse, doctor, physical therapist, etc.) administering treatment to the user, or any other third party assisting or treating the user. As discussed above, articulation of the lever arm (140,240,340,440) and movement of the cam (135,235,335,435) in 1410 causes a force to be applied to one or both ends of the flexible member (205,305,405) or one or both of the side arms (105,110) in 1415. In 1420, the force applied to one or both ends of the flexible member (205,305,405) or one or both of the side arms (105,110) is translated to a pressure applied to the at least one bone of the user or patient by the flexible member (205,305,405) or one or both of the side arms (105,110).

The specific strength of the applied pressure can be adjusted based on the relative length of the short bar (130,230,330,430). The specific values of pressure applied to the user's wrist may be specifically modulated and selected by a treating medical professional to ensure enough pressure is applied while also ensuring excessive pressure, which might cause temporary or permanent damage, may be prevented.

In 1425, after a sustained period of time, the lever arm (140,240,340,440) is returned to an initial position, reducing the force applied by the cam and thereby reducing the pressure applied to the user's wrist. The specific period of sustained pressure may be on the order of 30-90 seconds, or any duration as prescribed by a treating medical professional to ensure effective treatment.

While certain example implementations have been described, these example implementations have been presented by way of example only, and are not intended to limit the scope of the protection. Indeed, the novel methods and apparatuses described herein may be embodied in a variety of other forms. Furthermore, various omissions, substitutions and changes in the form of the methods and systems described herein may be made without departing from the spirit of the protection. The accompanying claims and their equivalents are intended to cover such forms or modifications as would fall within the scope and spirit of the protection.

The invention claimed is:

1. A device for applying pressure to at least one bone of a human arm, the device comprising:
 a first side arm having a first end and a second end;
 a second side arm having a first end and a second end;
 a linear member having a first end and a second end, the first end of the linear member being fixedly coupled to the second end of the first side arm and the second end of the linear member being slidingly coupled to the second end of the second side arm;
a cam pivotably coupled to the second end of the linear member, the cam contacting a surface of the second end of the second side arm;
a lever arm coupled to the cam, the lever arm being movable between:
a first position in which the lever arm positions the cam to apply a first pressure to the surface of the second end of the second side arm; at least one of the first side arm and the second side arm being configured to transmit the first pressure to the at least one bone of the human arm; and
a second position in which the lever arm positions the cam to apply a second, larger pressure to the surface of the second end of the second side arm causing the second end of the second side arm to move relative to second end of the linear member and reduce a distance between the second end of the first side arm and the second end of the second side arm; at least one of the first side arm and the second side arm being configured to transmit the second, larger pressure to the at least one bone of the human arm; and
a connecting piece hingedly connecting the first end of the first side arm to the first end of the second side arm, to pivotably couple the first end of the second side arm to the first end of the first side arm.

2. The device of claim 1, further comprising a padding member attached to at least one of the first side arm and the second side arm and the linear member.

3. The device of claim 1, wherein the at least one bone of the arm is at least one of a radius bone and an ulna bone.

4. A device for applying pressure to at least one bone of a human arm, the device comprising:
a first side arm having a first end and a second end;
a second side arm having a first end and a second end, the first end of the second side arm being pivotably coupled to the first end of first side arm;
a linear member having a first end and a second end, the first end of the linear member being connected to the second end of the first side arm, and the second end of the linear member slidingly connected to the second end of second side arm;
a cam pivotably coupled to the second end of the linear member, the cam contacting a the surface of the second end of the second side arm;
a lever arm coupled to the cam, the lever arm being movable between:
a first position in which the lever arm positions the cam member to apply a first pressure to the surface of the second end of second side arm; at least one of the first side arm and the second side arm being configured to transmit the first pressure to the at least one bone of the human arm by at least one of the first side arm and the second side arm; and
a second position in which the lever arm positions the cam member to apply a second, larger pressure to the surface of the second end of the second side arm and reduce a distance between the second end of the second side arm and the second end of the first side arm; at least one of the first side arm and the second side arm being configured to transmit the second, larger pressure to the at least one bone of the human arm by at least one of the first side arm and the second side arm; and
a connecting piece hingedly connecting the first end of the first side arm to the first end of the second side arm to pivotably couple the first end of the second side arm to the first end of the first side arm.

5. The device of claim 4, wherein the first end of at least one of the first side arm and the second side arm comprises a plurality of holes; and
wherein the device comprises at least one pin member configured to couple first end of the first side arm to the first end of the second side arm.

6. The device of claim 4, wherein the first end of at least one of the first side arm and the second side arm comprises a plurality of holes; and
wherein the connecting piece comprises at least one pin member configured to couple the connecting member to one of the plurality of holes formed in the first end of at least one of the first side arm and the second side arm.

7. The device of claim 4, further comprising:
a first swivel member attached to the second end of the first side arm, wherein the first swivel member is connected to a first end of the linear member.

8. The device of claim 7, further comprising a second swivel member attached to the second end of the second side arm, wherein the second swivel member is connected to a second end of the linear member.

9. The device of claim 4, further comprising a padding member attached to at least one of the first side arm, the second side arm, and the linear member.

10. The device of claim 4, wherein the at least one bone of the arm is at least one of a radius bone and an ulna bone.

11. A method of relieving carpal tunnel syndrome of a person comprising:
placing a device around the wrist of the person, the device including:
a first side arm having a first end and a second end;
a second side arm having a first end and a second end;
a linear member connecting the second end of the first side arm and the second end of the second side arm, and a lever arm coupled to a cam attached to one of the second end of the first side arm and the second end of the second side arm; and
a connecting piece hingedly connecting the first end of the first side arm to the first end of the second side arm to pivotably couple the first end of the second side arm to the first end of the first side arm;
articulating the lever arm to move the cam relative to one of the second end of the first side arm and the second end of the second side arm;
applying, by the movement of the cam, a force to one of the second end of the first side arm and the second end of the second side arm; and
applying, by the force applied to one of the second end of the first side arm and the second end of the second side arm, a pressure to at least one bone of the wrist of the person.

12. The method of claim 11, further comprising:
releasing the lever arm after the pressure has been applied to at least one bone of the wrist for a sustained period of time.

13. The device of claim 1, wherein the first end of at least one of the first side arm and the second side arm comprises a plurality of holes; and
wherein the connecting piece comprises at least one pin member configured to couple the connecting member to one of the plurality of holes formed in the first end of at least one of the first side arm and the second side arm.

* * * * *